United States Patent [19]
Henning et al.

[11] Patent Number: 6,155,992
[45] Date of Patent: Dec. 5, 2000

[54] METHOD AND APPARATUS FOR OBTAINING INTERSTITIAL FLUID FOR DIAGNOSTIC TESTS

[75] Inventors: Timothy P. Henning, Vernon Hills, Ill.; Robert G. Hiltibran, Bristol, Wis.; David D. Cunningham, Lake Villa, Ill.; Eric B. Shain, Glencoe, Ill.; Brian J. Tarkowski, Lake Villa, Ill.; Douglas F. Young, Grayslake, Ill.

[73] Assignee: Abbott Laboratories, Abbott Park, Ill.

[21] Appl. No.: 08/982,449

[22] Filed: Dec. 2, 1997

[51] Int. Cl.[7] .......................................................... A61B 5/00
[52] U.S. Cl. ............................................. 600/583; 606/182
[58] Field of Search ................................. 600/583, 573; 606/180–183

[56] References Cited

U.S. PATENT DOCUMENTS

| | | | |
|---|---|---|---|
| 3,811,442 | 5/1974 | Maroth | 606/180 |
| 4,627,445 | 12/1986 | Garcia et al. | 128/770 |
| 4,653,513 | 3/1987 | Dombrowski | 606/182 |
| 4,775,361 | 10/1988 | Jacques et al. | 604/20 |
| 4,844,098 | 7/1989 | Mitchen | 128/765 |
| 5,003,987 | 4/1991 | Grinwald | 128/734 |
| 5,161,532 | 11/1992 | Joseph | 128/635 |
| 5,165,418 | 11/1992 | Tankovich | 128/760 |
| 5,318,584 | 6/1994 | Lange et al. | 606/182 |
| 5,320,607 | 6/1994 | Ishibashi | 604/115 |
| 5,374,556 | 12/1994 | Bennett et al. | 435/287 |
| 5,383,917 | 1/1995 | Desai et al. | 607/702 |
| 5,509,410 | 4/1996 | Hill et al. | 128/637 |
| 5,554,153 | 9/1996 | Costello et al. | 606/9 |
| 5,680,872 | 10/1997 | Sesekura et al. | 128/760 |
| 5,746,217 | 5/1998 | Erickson et al. | 128/760 |

FOREIGN PATENT DOCUMENTS

| | | |
|---|---|---|
| 0449525 | 10/1991 | European Pat. Off. . |
| 0453283 | 10/1991 | European Pat. Off. . |
| 0595237 | 5/1994 | European Pat. Off. . |
| 0671146 | 9/1995 | European Pat. Off. . |
| 0797951 | 10/1997 | European Pat. Off. . |
| 8700413 | 1/1987 | WIPO . |
| 9409713 | 5/1994 | WIPO . |
| 9510223 | 4/1995 | WIPO . |
| 9707734 | 3/1997 | WIPO . |
| 9742883 | 11/1997 | WIPO . |
| 9824366 | 6/1998 | WIPO . |

OTHER PUBLICATIONS

L.J. Petersen et al., "Microdialysis of the Interstitial Water Space in Human Skin In Vivo: Quantitative Measurement of Cutaneous Glucose Concentrations", *The Journal of Investigative Dermatology*, vol. 99, No. 3, (1992), pp. 357–360.

A.L. Krogstad et al., "Microdialysis Methodology for the Measurement of Dermal Interstitial Fluid in Humans", *British Journal of Dermatology*, vol. 134, (1996), pp. 1005–1011.

F. Sternberg et al., "Subcutaneous Glucose Concentration in Humans: Real Estimation and Continous Monitoring", *Diabetes Care*, vol. 18, No. 9, (1995), pp. 1266–1269.

D.G. Maggs et al., "Interstitial Fluid Concentrations of Glycerol, Glucose, and Amino Acids in Human Quadricep Muscle and Adipose Tissue", *J. Clin. Inveat.*, vol. 96, (1995), pp. 370–377.

R.J. Lane et al., "Ultraviolet–Laser Ablation of the Skin", *IBM Research Report*, (1984).

*Primary Examiner*—Max Hindenburg
*Attorney, Agent, or Firm*—David L. Weinstein

[57] ABSTRACT

A method and apparatus for obtaining a sample of interstitial fluid from a patient for subsequent diagnostic tests, e.g., glucose monitoring. In one aspect of the invention, the method comprises the steps of (a) treating an area of the skin with vacuum or heat or both vacuum and heat to increase the availability of interstitial fluid at that area of the skin; (b) forming an opening in the treated area of the skin; and (c) extracting the sample of interstitial fluid from the opening in the skin, with the aid of vacuum and stretching of the skin. In another aspect of the invention, an apparatus for carrying out the method described previously is provided. Th apparatus comprises (a) a device for forming an unobstructed opening in the area of the skin from which the sample is to be extracted, preferably a lancing assembly; and (b) a vacuum pump. Preferably, the apparatus also includes a housing.

32 Claims, 4 Drawing Sheets

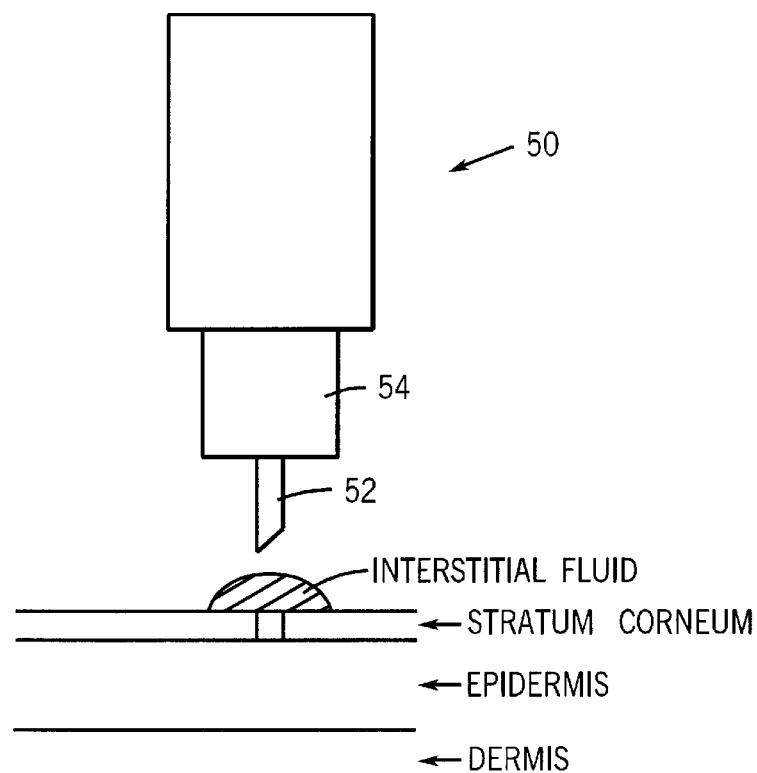
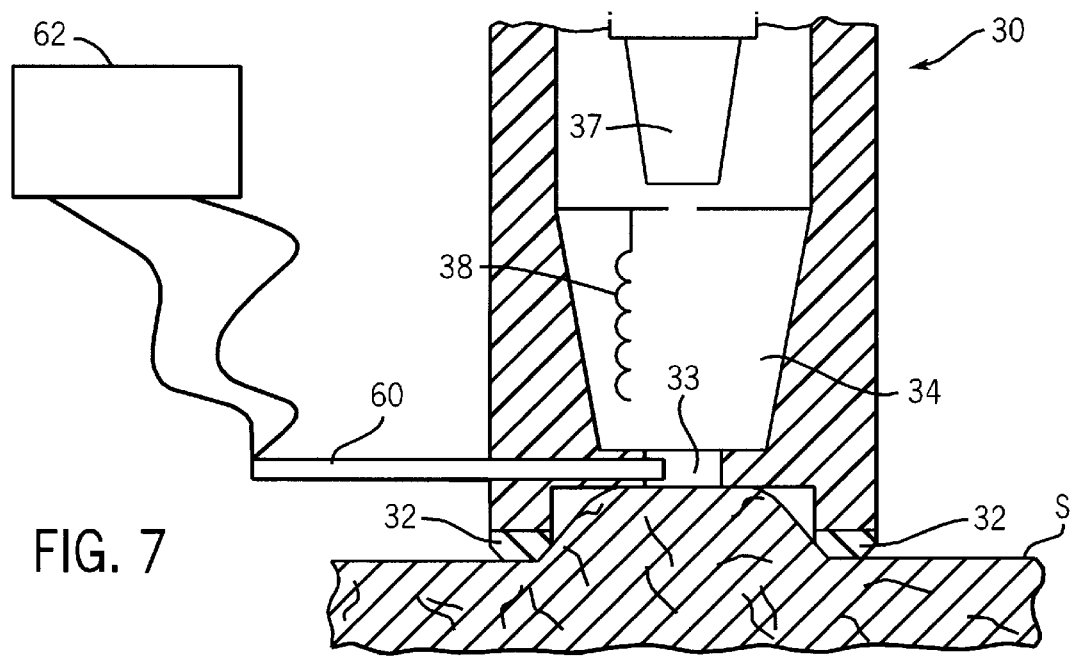

METHOD AND APPARATUS FOR OBTAINING INTERSTITIAL FLUID FOR DIAGNOSTIC TESTS

BACKGROUND OF THE INVENTION

1. Field of the Invention

This invention relates to a method and apparatus for obtaining samples of interstitial fluid for diagnostic purposes.

2. Discussion of the Art

The prevalence of diabetes has been increasing markedly in the world. At this time, diagnosed diabetics represented about 3% of the population of the United States. It is believed that the total actual number of diabetics in the United States is over 16,000,000. Diabetes can lead to numerous complications, such as, for example, retinopathy, nephropathy, and neuropathy.

The most important factor for reducing diabetes-associated complications is the maintenance of an appropriate level of glucose in the blood stream. The maintenance of the appropriate level of glucose in the blood stream may prevent and even reverse many of the effects of diabetes.

Glucose monitoring devices of the prior art have operated on the principle of taking blood from an individual by a variety of methods, such as by needle or lancet. An individual then coats a paper strip carrying chemistry with the blood, and finally insert the blood-coated strip into a blood glucose meter for measurement of glucose concentration by determination of change in reflectance.

There are numerous devices currently available for diabetics to monitor the level of blood glucose. The best of these devices require the diabetic to prick a finger and to collect a drop of blood for placement on a strip, which is inserted into a monitor that determines the level of glucose in the blood. Pricking one's finger tends to be painful. Moreover, a relatively large wound is produced by the pricking device, typically a lancet or a needle. It is known that the pain arising from the finger prick deters diabetics from compliance with the monitoring regimen. Lack of compliance increases the risk of complications due to diabetes. Thus there is a need for a more painless and less traumatic means of collecting biological samples for monitoring one's level of glucose in a biological fluid.

SUMMARY OF THE INVENTION

This invention provides a method and apparatus for obtaining a sample of interstitial fluid from a patient for subsequent diagnostic tests, e.g., glucose monitoring. It is believed that the concentration of glucose in interstitial fluid is correlated to the concentration of glucose in blood. In one aspect of the invention, the method comprises the steps of:

(a) treating an area of the skin with vacuum or heat or both vacuum and heat to increase the availablity of interstitial fluids at that area of the skin;

(b) forming an opening in the treated area of the skin; and (c) extracting the sample of interstitial fluid from the opening in the skin, with the aid of vacuum and stretching of the skin.

Step (b) is preceded by the step of increasing the availability of biological fluids in the portion of the skin from which the sample is to be extracted.

In one embodiment, the availability of biological fluids in the area of the skin from which the sample is to be extracted is increased, preferably by means of a vacuum, which is applied to the surface of the skin in the vicinity of the opening prior to forming the opening in the skin. The vacuum causes the portion of the skin in the vicinity of the interstitial fluid extraction site to become engorged with biological fluids, i.e., blood and interstitial fluid. The vacuum also causes the portion of the skin in the vicinity of the interstitial fluid extraction site to become stretched.

An opening in this stretched portion of skin can be formed with a cutting device, e.g., a rotating lancet, a rotating drill, or other device capable of forming an opening in the skin, e.g., a laser. If a cutting device is used to form the opening, it must be retracted from the opening prior to the step of extracting the sample of interstitial fluid from the opening. This retraction will allow the unrestricted flow of interstitial fluid through the opening. After the opening is formed, a vacuum is preferably used to aid in extracting the sample of interstitial fluid from the opening in the skin.

The sample can be analyzed from the drops of interstitial fluid that collect on the surface of the skin at the site of the opening by applying the interstitial fluid directly to a glucose detector. Alternatively, the sample be collected in such a manner, e.g., via a capillary tube, that it can be analyzed by conventional diagnostic devices, such as, for example, a biosensor. In another preferred embodiment, the sample can be collected in a collection zone that is integrated with a conventional diagnostic device, e.g., a biosensor.

In another embodiment of the method of this invention, the availability of interstitial fluid in the area of the skin from which the sample is to be extracted can be increased by means of applying thermal energy to that area of skin. The thermal energy causes the interstitial fluids in that area of the skin to flow more rapidly, thereby allowing more interstitial fluid to be collected per given unit of time. In this alternative embodiment, steps (b) and (c) can be carried out in the same manner as they were carried out in the embodiment where a vacuum is used to treat the skin prior to forming the opening.

In another aspect of the invention, an apparatus for collecting a sample of interstitial fluid for analysis in a diagnostic test is provided. In a preferred embodiment, the apparatus comprises:

(a) a housing;

(b) a device for forming an unobstructed opening in an area of skin from which said sample is to be extracted, preferably a rotating drill or a rotating lancet; and (c) a vacuum pump.

It is also possible to dispense with the housing. However, the housing is preferred for the convenience of the patient and the protection of the components.

The vacuum pump and the opening-forming device, e.g., a rotating drill or a rotating lancet, require a source of power. If the apparatus includes a housing, the source of power can be disposed within the housing. Alternatively, the source of power can be external to the housing.

The preferred device for forming an unobstructed opening in the area of the skin from which the sample of interstitial fluid is to be extracted is a lancing assembly, which preferably comprises a rotating drill or a rotating lancet, for forming an opening in the skin. Alternatively, the unobstructed opening in the skin can be formed by a laser.

The vacuum pump can serve the dual purposes of (1) stretching the skin and (2) enhancing the extraction of the sample of interstitial fluid from the unobstructed opening in the skin. Preferably, the vacuum pump can serve the purposes of (1) stretching the skin, (2) increasing the availability of biological fluids to the area of the skin from which the sample is to be extracted, (3) holding the skin in precise position for accurate cutting by means of a cutting tool, and (4) enhancing the extraction of the sample of interstitial fluid from the unobstructed opening in the skin. Preferably, the housing further contains electronics having programmed instructions to switch the vacuum pump on and off to maintain the desired level of vacuum.

The apparatus preferably contains a motor for driving the rotating drill or rotating lancet, valves, such as, for example, solenoid valves, for releasing the vacuum at the conclusion of the interstitial fluid extraction procedure. The apparatus can optionally contain a heating element to increase the availability of biological fluids to the area of the skin from which the sample is to be extracted. The apparatus can also contain a glucose detector integrated with the apparatus, e.g., a biosensor, to analyze the sample of interstitial fluid collected by the apparatus.

The method and apparatus of this invention provide several advantages over the methods and apparatus of the prior art. First, a sufficient amount of interstitial fluid for conducting glucose monitoring tests can be extracted from parts of the body. Thus, by rendering parts of the body suitable for extracting interstitial fluid, the use of a painful finger lance for extracting blood can be avoided. Second, by increasing the availability of biological fluids at the site where the interstitial fluid is to be extracted, the period of time required for extracting the sample can be reduced. Because of these advantages, the diabetic patient is more likely to monitor glucose levels in a biological fluid at the intervals prescribed by his doctor.

BRIEF DESCRIPTION OF THE DRAWINGS

FIG. 3 also illustrates the spatial relationship between the nosepiece of the lancing assembly and a glucose detector, e.g., a biosensor.

FIGS. 6A, 6B, and 6C are schematic diagrams illustrating the position of the lancet relative to the surface of the skin prior to, during and after the lancing step of the method of this invention.

FIG. 7 is a schematic diagram illustrating how a vacuum causes a portion of the skin to become stretched prior to the formation of an opening in the skin from which the sample of interstitial fluid is extracted. FIG. 7 also illustrates a laser and a heating element.

DETAILED DESCRIPTION

Figure 1A:
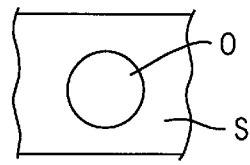
FIG. 1A is a plan view of an opening, greatly enlarged, in the stratum corneum formed by a rotating drill.

As used herein, the expression "interstitial fluid" means the substantially clear, substantially colorless fluid found in the human body, which occupies the space between the cells of the human body. The term "drill" means an implement with cutting edges or a pointed end for boring holes in the skin, usually by rotating abrasion. The term "lancet" means a medical implement having a multi-faceted blade.

The embodiments of this invention require the following steps to carry out the function of obtaining a sample of interstitial fluid for carrying out a diagnostic test, e.g., glucose monitoring:

(a) treating an area of the skin with vacuum or heat or both vacuum and heat to increase the availablity of interstitial fluid at that area of the skin;

(b) forming an unobstructed opening in the treated area of the skin; and (c) extracting the sample of interstitial fluid from the opening in the skin, with the aid of vacuum and stretching of the skin.

In the preferred embodiment of this invention, step (b), the step of forming the unobstructed opening, is preceded by the step of increasing the availability of interstitial fluid at the area of the skin from which the sample is to be extracted. The availability of interstitial fluids at a given area of the skin can be increased by at least two methods. In one method, a vacuum can be used to cause interstitial fluid to pool in the area of the skin where the vacuum is applied. In another method, heat can be used to cause interstitial fluid to flow more rapidly in the area of the skin where heat is applied, thereby allowing a greater quantity of interstitial fluid to be extracted from the interstitial fluid extraction site per unit of time. The combination of vacuum and heat can also be used.

Elements for increasing the availability of interstitial fluid at an interstitial fluid extraction site that are suitable for use in this invention include, but are not limited to, a vacuum pump, a localized heating element, skin stretching element, and chemicals. As stated previously, applying a vacuum to the area of the skin from which interstitial fluid is to be extracted can increase interstitial fluid availability under and within the skin at the application site. The vacuum can also be used to stretch the skin upwardly into a chamber, thereby increasing pooling of interstitial fluid under the skin. This combination of vacuum and skin stretching can also be used to extract interstitial fluid from the opening in the skin. It is well-known that heat can increase perfusion on the large scale of a limb. Chemical means, such as histamine, can be used to cause a physiological response to increase perfusion under and within the skin.

The step of forming an unobstructed opening in the area of the skin from which the sample of interstitial fluid is to be extracted is carried out by a cutting device or some other type of device capable of forming an unobstructed opening in the skin. Cutting devices suitable for this invention include, but are not limited to, mechanical lancing assemblies. Mechanical lancing assemblies suitable for use in this invention, include, but are not limited to, rotating opening-forming devices, such as, for example, rotating drills and rotating lancets. Rotating devices are particularly preferred because the depth of cut obtained from these devices is more controllable than the depth of cut obtainable from conventional lancets. The skin is very elastic and will deform when struck by the lancet. The lancet will penetrate the skin, but the depth of penetration is not easily controllable because this deformation of the skin is not reproducible. Conventional lancing devices are designed to penetrate much deeper than necessary because of the variability in the deformation of the skin to lancing. A lancet need only penetrate from 0.2 to 0.5 mm into the skin to reach the capillary loops of the skin's dermal layer. The standard depth of lancet penetration is 1.6 mm. In order to assure that capillaries are reached the lancet must be fired much deeper than theoretically necessary. The depth setting of lancet penetration may be deeper than the preferred 0.2 mm to 0.5 mm, because the skin deforms when it is contacted by the rotary drill or lancet. The depth setting does not indicate the actual depth of penetration into the skin. The depth setting takes into account a combination of factors including deformation and depth of penetration into the skin. Thus, a conventional lancing device cannot be used to reliably make the shallow openings in the skin that would be necessary to obtain interstitial fluid without penetrating to the dermal layer and obtaining blood. Rotating the lancet or using a drill bit to form the opening in the stratum corneum provides a means of forming a shallow opening. The act of rotation with a cutting tool is known to form openings in materials by abrading the surface of the material. By utilizing rotation with a lancet or drill, a shallow opening can be formed reproducibly in the skin, thereby allowing the interstitial fluid to be obtained without contamination by blood. The formation of an opening in the stratum corneum that does not reach the dermis has the added benefit of being painless. The nerve endings are located in the dermal layer, and, consequently, no pain response is encountered if the dermal layer is not abraded. Rotating devices can be closely controlled by specifying the following parameters:

(1) depth setting;
(2) revolutions per minute setting;
(3) diameter of drill bit setting;
(4) duration of drilling.

The depth of cut must be sufficiently great to penetrate the stratum corneum, but must also be sufficiently low to avoid piercing capillaries. With respect to revolutions per minute, this setting must be sufficiently high to avoid inducing pain in the patient, but must also be sufficiently low to avoid burning the flesh of the patient. The diameter of the drill bit must be sufficiently large to bore an opening or openings of sufficient diameter to allow extraction of at least about 0.25 microliters of interstitial fluid within about five minutes or less, but must be sufficiently small so that the opening or openings bored will be of low enough diameter to heal within about seven days, preferably about four days, more preferably about two days. The application of time setting must be sufficiently high to ascertain that the proper depth is reached but must be sufficiently low that only the stratum corneum is pierced and at most an insubstantial amount of capillaries are pierced. Representative examples of settings suitable for use with a rotating drill are as follows:

| Parameter setting | Acceptable range | Preferred range |
| --- | --- | --- |
| Depth | 0.1–2.0 mm | 0.8–1.1 mm |
| Revolutions per minute | 50–10,000 rpm | 1500–1800 rpm |
| Diameter of drill bit | 0.2–2.0 mm | 0.7 mm |

Figure 1B:
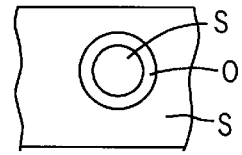
FIG. 1B is a plan view of an opening, greatly enlarged, in the stratum corneum formed by a rotating lancet.

Rotating drills are sometimes preferred over rotating lancets because rotating drills form an opening of the type shown in FIG. 1A, whereas rotating lancets form an opening of the type shown in FIG. 1B. In both FIGS. 1A and 1B, the letter "S" represents the skin, and the letter "O" represents the opening in the skin.

Other types of devices capable of forming an unobstructed opening in the skin include, but are not limited to, lasers. Lasers suitable for forming an unobstructed opening in the skin to draw blood are also well-known in the art. See for example, U.S. Pat. Nos. 4,775,361, 5,165,418, 5,374,556, International Publication Number WO 94/09713, Lane et al. (1984) IBM Research Report—"Ultraviolet-Laser Ablation of Skin", and PCT/US96/113865, all of which are incorporated herein by reference. Lasers that are suitable for forming an unobstructed opening in the skin the skin include Er:YAG, Nd:YAG, and semiconductor lasers. Other types of devices capable of forming an unobstructed opening in the skin can be used, and this disclosure should not be construed so as to be limited to the devices listed.

Regardless of what type of device is utilized to form an unobstructed opening in the skin, the opening formed by the device must be unobstructed. As used herein, the term "unobstructed" means free from clogging, hampering, blocking, or closing up by an obstacle. More specifically, the expressions "unobstructed opening in the area of the skin from which the sample is to be extracted", "unobstructed opening in the skin", and the like are intended to mean that the portion of the opening below the surface of the skin is free from any foreign object that would clog, hamper, block, or close up the opening, such as, for example, a drill bit from a rotating drill or a lancet from a rotating lancet. For example, if a rotating drill is used to form the opening, the drill bit must be retracted from the opening prior to the commencement of the extraction of interstitial fluid. Because lasers do not require contact with the skin to form openings in the skin, this type of device typically provides unobstructed openings. However, these expressions are not intended to include foreign objects at the surface of the skin or above the surface of the skin, such as, for example, a glucose monitor, e.g., a biosensor strip. In addition, the requirement of an unobstructed opening exposes the body to a foreign object either not at all or for only a very short period of time, which is welcomed by the patient.

The step of extracting the sample of interstitial fluid from the opening in the skin is preferably carried out by a combination of extraction enhancing elements. Extraction enhancing elements suitable for use in this invention include, but are not limited to, vacuum, skin stretching elements, and heating elements. It has been discovered that when these elements are used in combination, the volume of interstitial fluid extracted is greatly increased, particularly when a vacuum is applied in combination with skin stretching. In this combination, the vacuum not only causes the interstitial fluid to be rapidly removed from the unobstructed opening by suction, it also causes a portion of the skin in the vicinity of the opening to be stretched. Stretching of the skin can be effected by other means, such as mechanical means or adhesives. Mechanical means include devices for pinching or pulling the skin; adhesives bring about stretching of the skin by means of pulling. It is preferred to use a vacuum to effect stretching of the skin. Like a vacuum, a heating element operates more effectively in combination with other techniques, e.g., stretching of the skin. It is also possible to combine vacuum with heating or to combine vacuum with heating and skin stretching.

In the preferred embodiments of the invention, the extracted interstitial fluid is also collected. The step of collecting the sample of interstitial fluid can be carried out in a variety of ways. For example, the interstitial fluid can be collected in capillary tubes or absorbent paper. Alternatively, the interstitial fluid can be allowed to remain in the interstitial fluid collection chamber, from which it can used directly in a diagnostic test. Most preferably, the sample of interstitial fluid is collected on the application zone of a glucose detector, from where it can be used to provide an indication of the concentration of glucose in the blood. As stated previously, it is believed that the concentration of glucose in interstitial fluid is correlated to the concentration of glucose in blood. Regardless of the manner in which the interstitial fluid sample is collected, the sample can be analyzed at a time later than the time of collection or at a location remote from the location of collection or both.

Figure 2:
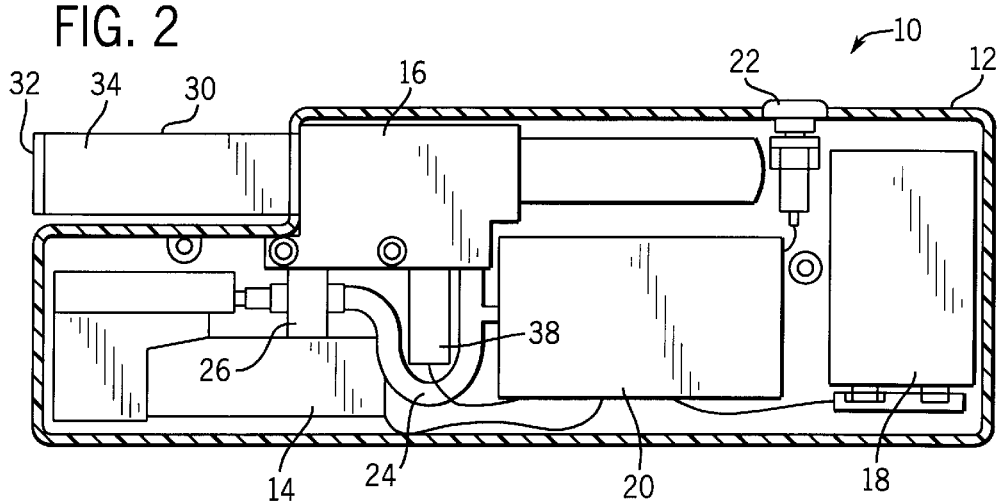
FIG. 2 is a plan view of the components of a preferred embodiment of the apparatus of this invention. In this figure, the cover of the housing is removed.

A preferred embodiment of the invention will now be described in detail. referring now to FIG. 2, interstitial fluid extraction device 10 comprises a housing 12. Disposed within the housing 12 are a vacuum pump 14, a lancing assembly 16 containing a rotating drill (not shown), a battery 18, and electronics 20. A switch 22 is provided to activate electronics 20. A motor (not shown) is provided to operate the rotating drill of the lancing assembly 16.

The housing 12 is preferably made from a plastic material. It is preferably of sufficient size to contain all of the components that are required for forming an unobstructed opening in the area of the skin from which the sample of interstitial fluid is to be extracted, extracting the sample of interstitial fluid from the unobstructed opening in the skin, preferably with the aid of a vacuum and a stretching of the skin, and collecting the extracted sample in an amount sufficient to carry out a diagnostic test. Methods of preparing the housing 12 are well-known to one of ordinary skill in the art. As stated previously, the housing 12 is not required, but is preferred for the convenience of the patient and the protection of the components.

The vacuum pump 14 must be capable of providing a vacuum that will provide sufficient suction to stretch the portion of the skin in the region from which the sample of interstitial fluid is to be extracted. Typically, the portion of stretched skin is raised a distance of 1 to 10 mm, preferably 3 to 5 mm, from the plane of the body part of which it is a portion. As the suction provided by the vacuum pump 14 is stretching the appropriate portion of skin, the suction provided by the vacuum pump 14 also causes the stretched portion to become engorged with interstitial fluid. The level of suction provided must be sufficient to cause a relatively large volume of interstitial fluid to become engorged at the point that the vacuum is applied. The vacuum pump 14 must also be capable of providing sufficient suction to extract interstitial fluid from the opening in the skin at a rate sufficient to extract at least 0.25 $\mu$L of interstitial fluid within a period of five minutes, preferably within a period of two minutes. A vacuum pump 14 that is suitable for the device of this invention can be a diaphragm pump, a piston pump, a rotary vane pump, or any other pump that will perform the required functions set forth previously. Typically, the vacuum pump 14 employs a self-contained permanent magnet DC motor. Vacuum pumps that are suitable for this invention are well-known to those of ordinary skill in the art and are commercially available. A vacuum pump suitable for use in the present invention is available from T-Squared Manufacturing Company, Nutley, N.J., and has the part number T2-03.08.004.

The vacuum pump 14 is preferably capable of providing a pressure of down to about −14.7 psig, and is more preferably operated at from about −3.0 psig to about −10.0 psig. The area of the skin subjected to vacuum preferably ranges up to about 50 cm$^2$, more preferably from about 0.1 to about 5.0 cm$^2$. The period of vacuum application prior to forming the opening in the skin, i.e., for increasing the availability of interstitial fluid to the application site, preferably ranges up to about 5 minutes, preferably from about 1 to about 60 seconds. The period of vacuum application subsequent to forming the opening in the skin, i.e., for aiding in the extraction of interstitial fluid from the unobstructed opening, preferably ranges up to about 5 minutes, preferably from about 1 to about 120 seconds. The vacuum provided by the vacuum pump 14 can be continuous or pulsed. A continuous vacuum is preferred for the reason that it requires fewer components than does a pulsed vacuum. It is preferred that the vacuum applied not cause irreversible damage to the skin. It is preferred that the vacuum applied not produce bruises and discolorations of the skin that persist for several days. It is also preferred that the level of vacuum applied and duration of application of vacuum not be so excessive that it causes the dermis to separate from the epidermis, which results in the formation of a blister filled with fluid.

The lancing assembly 16 preferably comprises a rotating cutting element, preferably a rotating drill or a rotating lancet. See FIG. 5. In the case of a drill, narrow gauge (28 to 30 gauge) drill bits are preferred. Drill bits and lancet needles suitable for this invention can be made from metal or plastic. The depth of penetration of the rotating cutting element preferably ranges from about 0.1 mm to about 1.5 mm, more preferably from about 0.1 mm to about 1.0 mm.

Lancing assemblies utilizing a rotating cutting element as described herein have never been used in the art. Any lancing assembly selected should operate in conjunction with the other features of the apparatus of this invention. For example, if a vacuum is employed, the lancing assembly must be designed so that a vacuum can be formed and drawn through the assembly.

The vacuum pump 14 is connected to the lancing assembly 16 by an evacuation tube 24. The air that is evacuated from the lancing assembly 16 by the vacuum pump 14 is removed via the evacuation tube 24. The evacuation tube 24 is typically made from a polymeric material. A check valve 26 is placed between the vacuum pump 14 and the lancing assembly 16 at a point in the evacuation tube 24 to prevent air removed from the lancing assembly 16 by the vacuum pump 14 from flowing back to the lancing assembly 16 and adversely affecting the vacuum.

A source of power for the vacuum pump 14 and the motor that runs the rotating cutting element can be disposed within the housing 12. A source of power suitable for the device of this invention is a battery 18. Alternatively, an external source of power can be used to operate the vacuum pump 14 and the motor that runs the rotating cutting element. The power source is actuated by the electronics 20, which, in turn, is actuated by the switch 22.

The electronics 20 may incorporate a microprocessor or microcontroller. The function of the electronics 20 is to switch power on and off to operate the various components in the apparatus. These components include, but are not limited to, the vacuum pump 14. The electronics 20 can also be use to switch power on and off to operate components in alternative embodiments, e.g., heating elements, lancing assemblies, indicating devices, motors, and valves. Electronics suitable for this invention is the "TATTLETALE MODEL 5F" controller/data logger, commercially available from Onset Computer Corporation, 536 MacArthur Blvd. P.O. Box 3450, Pocasset, Mass. 02559-3450. Auxiliary electronic devices, such as power transistors, pressure monitors, and OP-Amps (operational amplifiers), may also be required in order to provide an interface between the controller and the operational components. All electronics required for this invention are well-known to one of ordinary skill in the art and are commercially available. Auxiliary electronic devices suitable for use in this invention include the components listed in Table 1.

TABLE 1

| Component | Source | Catalog Number |
|---|---|---|
| Mosfet Drivers | International Rectifier El Segundo, CA | IRLD024 |
| Op-Amp | National Semiconductor Santa Clara, CA | LM358 |
| Status LED | Hewlett-Packard Newark Electronics Schaumburg, IL | HLMPD150 |

TABLE 1-continued

| Component | Source | Catalog Number |
|---|---|---|
| Pressure Sensor | Sensym, Inc. Milpitas, CA | SDX15D4 |
| Motor | Portescap U.S. Inc. Hauppage, NY | ESCAP 2Z |

Figure 4:
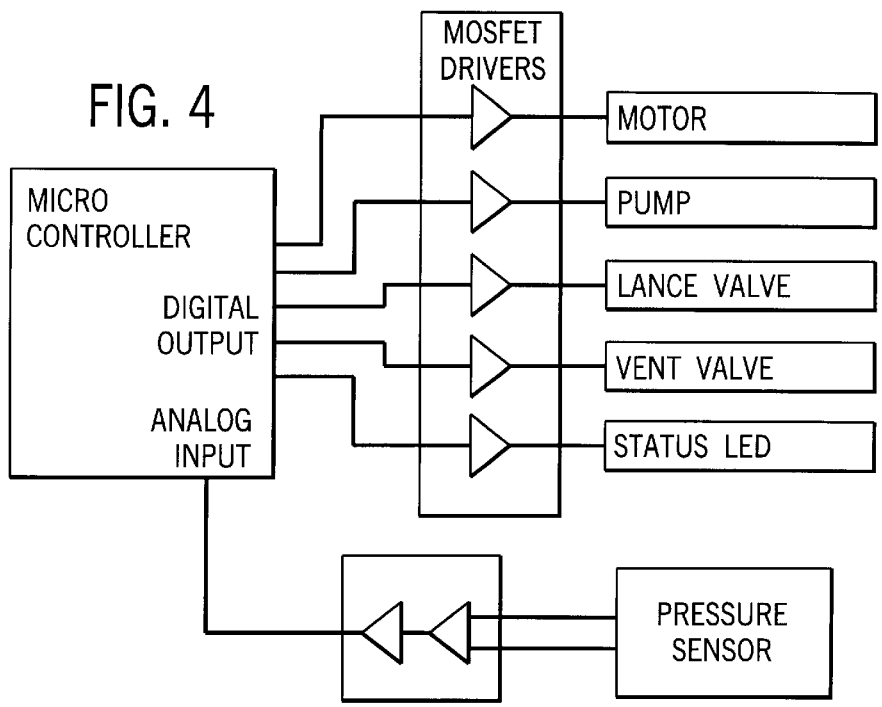
FIG. 4 is a block diagram illustrating the electronics of the preferred embodiment.

FIG. 4 illustrates by way of a block diagram how the foregoing electronic components can be arranged to carry out the method of the present invention.

Operation of the interstitial fluid extraction device 10 will now be described. Referring now to FIGS. 2, 3, 4, 5, 6A, 6B, and 6C, the nosepiece 30 of the lancing assembly 16 is applied to the surface of the skin, designated herein by the letter "S". The end of the nosepiece 30 that contacts the skin is equipped with a seal 32. The purpose of the seal 32 is to prevent air from leaking into interstitial fluid extraction chamber 34, so that the vacuum pump 14 can provide sufficient suction action for increasing the availability of interstitial fluid to the area of the skin from which the sample is to be extracted, stretching the skin, and extracting the sample of interstitial fluid from the unobstructed opening in the skin. The seal 32 surrounds an opening 33 in the nosepiece 30. The opening 33 in the nosepiece allows communication between the surface of the skin and a interstitial fluid extraction chamber 34 in the nosepiece 30. The seal 32 is preferably made of a rubber or an elastomeric material.

The switch 22 is actuated, typically by being pressed, thereby activating the electronics 20, which starts the vacuum pump 14. The vacuum pump 14 then provides a suction action. The suction action of the vacuum pump 14 causes the skin circumscribed by the seal 32 to become engorged with interstitial fluid. Engorgement of the skin with interstitial fluid is accompanied by a stretching of and rising up of the skin up to opening 33.

After an appropriate period of time, which is typically pre-set by the programmer of the electronics, the lancing assembly 16 is actuated, thereby causing the rotating cutting element 36 to first rotate at the proper rotational speed and then to abrade the skin that has risen up to the opening 33. The rotating cutting element 36 is caused to rotate at the proper rotational speed prior to being allowed to abrade the skin. The rotating cutting element 36 is then retracted, preferably automatically. Thereupon, the interstitial fluid flows out of the unobstructed opening resulting from the rotating cutting element 36, and, aided by the vacuum generated by the vacuum pump 14, is collected. When sufficient interstitial fluid has been collected or a pre-set time interval has passed, the electronics 20 causes the vacuum pump 14 to stop. The device 10 can then be removed from the surface of the skin after another solenoid valve (not shown because it is hidden under solenoid valve 38) is opened to vent the vacuum to allow ease of removal of the device from the surface of the skin. Solenoid valves suitable for use with the apparatus described herein are commercially available from The Lee Company, Essex, Conn. and have the part number LHDA0511111H.

Figure 5:
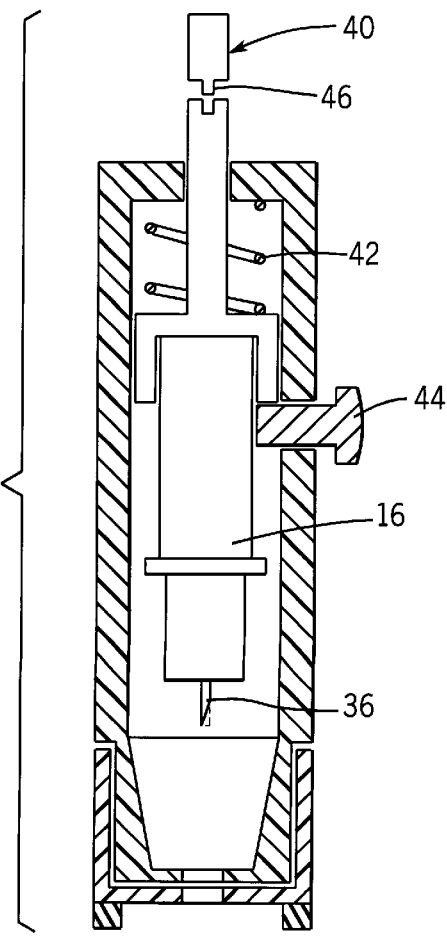
FIG. 5 is cross-sectional view of a lancing assembly suitable for use in this invention.

Referring now to FIG. 5, in embodiments utilizing a rotating lancet, the lancing assembly 16 preferably has a drive system 40 to bring about rotation of the lancet 36, a spring 42 to drive the lancet 36, and a release button 44 to allow the rotating lancet 36 to be released, whereby the rotating lancet 36 can penetrate the skin. The drive system 40 includes a clutch 46 to disengage when the rotating lancet 36 is projected upon actuation of the release button 44. In embodiments utilizing a rotating drill bit, the spring 42 and the release button 44 are not needed.

Figure 6A:
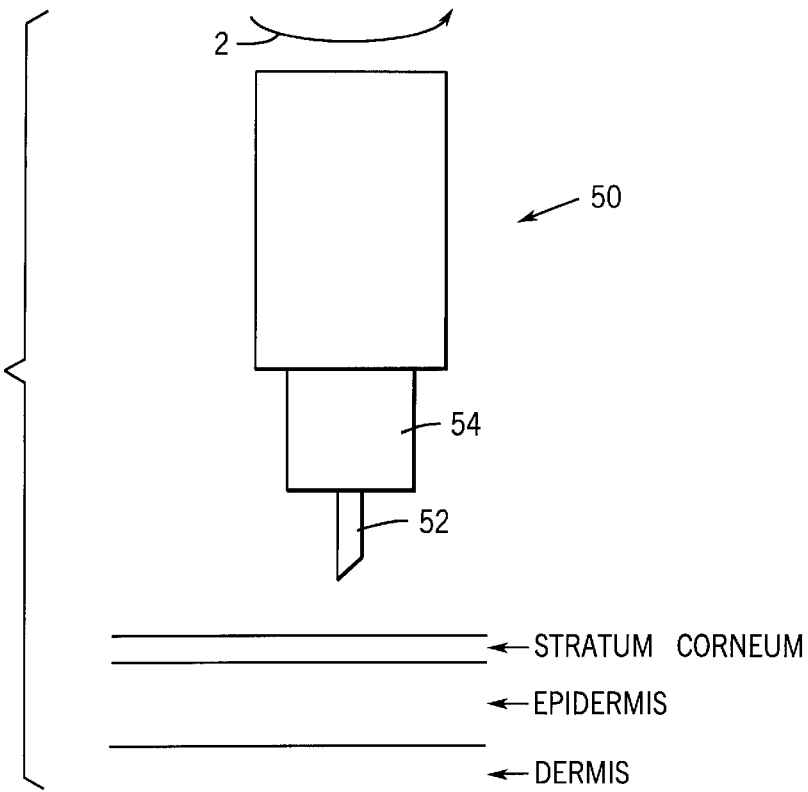
Figure 6B:
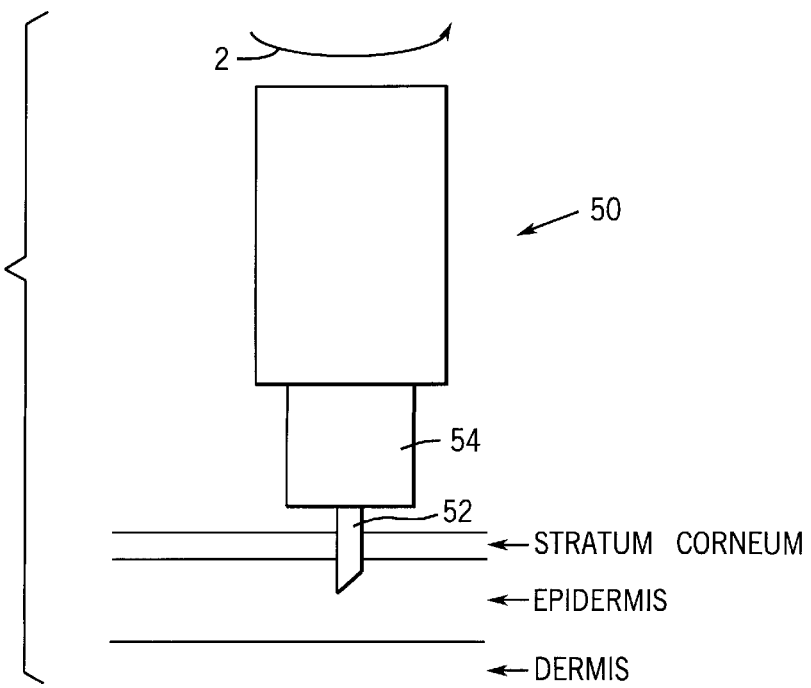

FIGS. 6A, 6B, and 6C illustrate schematically the positioning of the lancet assembly 50 of the apparatus of this invention before, during, and after the formation of an unobstructed opening in the skin for the purpose of obtaining intestitial fluid. FIG. 6A shows the position of the lancing assembly 50 before formation of the opening; FIG. 6B shows the position of the lancing assembly 50 during formation of the opening; FIG. 6C shows the position of the lancing assembly 50 after formation of the opening. In FIGS. 6A, 6B, and 6C, the lancet of the lancing assembly 50 is designated by the reference numeral 52 and the lancet holder of the lancing assembly 50 is designated by the reference numeral 54. In FIGS. 6A and 6B, the direction of rotation of the rotating lancet is indicated by the arrow "Z".

The interstitial fluid is preferably directly collected on the application zone of a glucose detector 60, e.g., a reflectance strip or biosensor. The interstitial fluid can then be used as the sample for a determination of glucose concentration in blood. It is believed that the concentration of glucose in blood is correlated to the concentration of glucose in interstitial fluid. Alternatively, the interstitial fluid can be collected by other collection devices, such as, for example, a capillary tube or absorbent paper.

The apparatus of the present invention can include a glucose detector for analyzing the fluid sample obtained by the apparatus. Glucose detectors are well-known in the art. With respect to glucose monitoring, there are two major categories of glucose detectors—optical detectors, e.g., reflectance strips, and electrochemical detectors, e.g., biosensors. Representative examples of reflectometers suitable for this invention are described in U.S. Pat. No. 4,627,445, incorporated herein by reference. Representative examples of biosensors suitable for this invention are described in U.S. Pat. No. 5,509,410, incorporated herein by reference. The glucose detector 60 can employ a meter 62, e.g., an optical meter or an electrochemical meter.

The glucose detector is preferably disposed in or near the nosepiece 30 of the lancing assembly 16. The glucose detector must be located at a position sufficiently close to the site of fluid extraction so that the quantity of extracted fluid collected will be sufficient to carry out a standard glucose determination. Typically, this distance will preferably be no more than 5 mm from the site of fluid extraction, more preferably no more than 3 mm from the site of fluid extraction, most preferably no more than 1 mm from the site of fluid extraction. Care must be taken in the placement of the glucose detector so that the detector does not adversely affect the vacuum, when a vacuum is employed to aid in the extraction of fluid. In addition, the glucose detector 60 can be modified, if necessary, so that the interstitial fluid collected in the collection zone of the glucose detector is capable of being used to activate the glucose detector.

Figure 3:
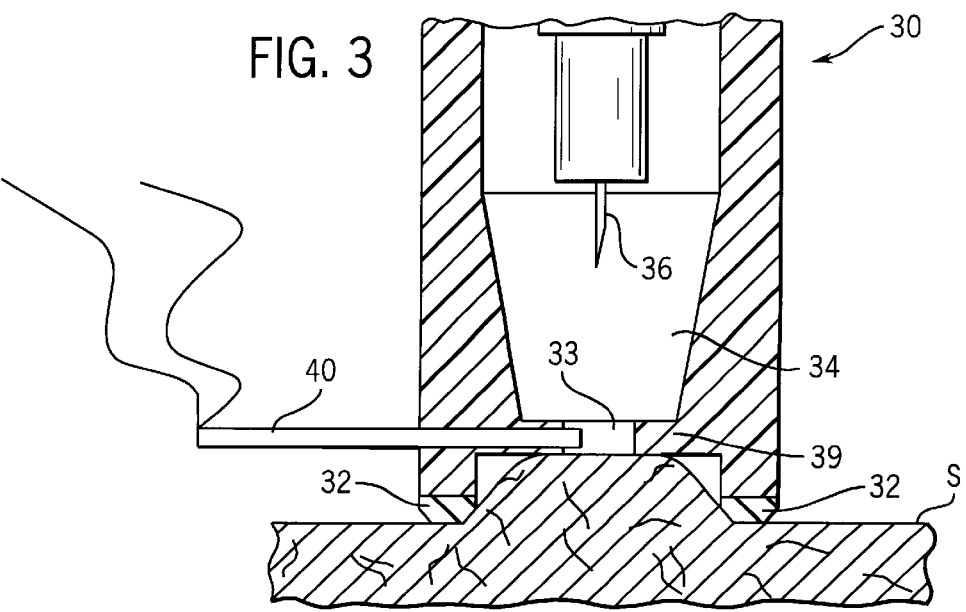
FIG. 3 is a schematic diagram illustrating how a vacuum causes a portion of the skin to become stretched prior to the formation of an opening in the skin from which the sample of interstitial fluid is extracted.

FIG. 3 also illustrates a manner for disposing a glucose detector 60 in the nosepiece 30 of the lancing assembly 16.

FIG. 7 illustrates an apparatus identical to that of FIG. 3, with the only differences being that the rotating cutting element 36 is replaced by a laser 37, and a heating element 38 has been added. The remaining components of the apparatus in FIG. 7 remain unchanged from those of FIG. 3.

This invention provides numerous advantages over fluid extraction devices of the prior art. Among these advantages are the following:

1. Ability to use numerous parts of the body as a site for the extraction of interstitial fluid;
2. Reduction of pain by eliminating the need to lance the finger;
3. Increase in speed of collection of fluid samples by means of pre-treatment comprising a combination of stretching of the skin in conjunction with heat or vacuum or both heat and vacuum;
4. Incorporation of glucose detector in apparatus for extracting the fluid sample.

The following examples illustrate various features of the present invention but is not intended to in any way limit the scope of the invention as set forth in the claims.

EXAMPLES

Example 1

This example illustrates that application of vacuum prior to formation of the opening as well as after formation of the opening results in a greater volume of interstitial fluid obtained than does the application of vacuum only after formation of the opening.

The apparatus included a small drill press (Electro-Mechanico, model 106 W) with a stationary platform for steadying and centering the arm below the drill head. Through the top of the platform was a 1.25 inch diameter opening with a clear plastic fitting that mounted flush with the bottom of the platform. In the clear plastic fitting a small opening that was just larger than the drill bit being used was centered to the drill head. The clear fitting allowed visual centering of the area at which the stratum corneum was to be opened. The depth of drill penetration was set at 1.08 mm below the bottom platform (depth setting determined experimentally to give good results) and the drill speed was set at 1691 rpm. The drill bit selected was a 0.74 mm stainless steel twist drill.

Sites on the upper forearm that were to have the openings formed were initially not pretreated with any form of vacuum or heat. These sites were compared directly to sites that were pretreated with heat (45° C.) and vacuum (−10 psig) for 60 seconds over an area of 10 square millimeters. The area was then pressed tightly up and centered under the clear plastic fitting, the drill head and bit lowered, and the top layer of skin opened with a 3 second application of the rotating drill bit. Vacuum (−10 psig) was reapplied to the opened area for 60 seconds by using a plastic fitting having an opening of diameter of 14.29 mm. Visual inspection of the drilled site was carried out using a 20× binocular telescope with recovery, and quantitation of the intersitial fluid was carried out using a 1 µl capillary pipette. The microcapillary pipette was touched into the area interstitial fluid was seen, and the fluid moved into the pipette by capillary action. Measuring the length of interstitial fluid in the pipette enabled the calculation of the volumes (in microliters) of interstitial fluid recovered. The results of this example are set forth in Table 2.

TABLE 2

|  | No pretreatment | Pretreatment |
|---|---|---|
| Average volume collected (microliters) | 0 | 0.1328 |
| Standard deviation (n = 4) | 0 | 0.0534 |

Example 2

This example illustrates that the application of vacuum with stretching of the skin results in a greater volume of interstitial fluid being obtained after formation of the opening. Decreasing the size of the area to which vacuum is applied for the collection of interstitial fluid results in a decrease in recovery of interstitial fluid.

The apparatus, the pretreatment, and the forming of the opening in the skin were carried out as described in Example 1. Plastic vacuum collection fittings were used. One fitting had a 7.5 mm diameter opening without mesh, and two fittings had 14.29 mm diameter openings, one without mesh and one with a 2 mm×2 mm mesh across the opening. The effect of stretching the skin and the effect of the area of applied vacuum can be assessed by the volumes of interstitial fluid recovered. The results of recovery of interstial fluid are set forth in Table 3.

TABLE 3

|  | Opening = 14.29 mm; mesh used | Opening = 14.29 mm; mesh not used | Opening = 7.5 mm; mesh not used |
|---|---|---|---|
| Average volume collected (µl) | 0 | 0.1328 | 0.0508 |
| Standard deviation (n = 4) | 0 | 0.0534 | 0.0149 |
| µl/sec/area (mm$^2$) | 0 | $1.38 \times 10^{-5}$ | $1.92 \times 10^{-5}$ |

The data in Table 2 show that the use of vacuum and skin stretching is necessary to obtain a sufficient amount of interstitial fluid from a patient.

Various modifications and alterations of this invention will become apparent to those skilled in the art without departing from the scope and spirit of this invention, and it should be understood that this invention is not to be unduly limited to the illustrative embodiments set forth herein.

What is claimed is:

1. A method for obtaining a sample of interstitial fluid for a diagnostic test, said method comprising the steps of:
   (a) treating an area of the skin with vacuum or heat or both vacuum and heat to increase the availability of interstitial fluid at that area of the skin;
   (b) forming an unobstructed opening in the treated area of the skin; and
   (c) extracting the sample of interstitial fluid from the unobstructed opening in the skin, with the aid of vacuum and stretching of the skin.

2. The method of claim 1, wherein said diagnostic test is a test to determine the concentration of glucose in a biological fluid.

3. The method of claim 1, further comprising the step of increasing the availability of interstitial fluid to said area of said skin from which said sample is to be extracted prior to forming said opening in said area of said skin from which said sample is to be extracted.

4. The method of claim 3, wherein a vacuum is used to increase the availability of interstitial fluid to said area of said skin from which said sample is to be extracted prior to forming said opening in said area of said skin from which said sample is to be extracted.

5. The method of claim 4, wherein stretching is used to increase the availability of interstitial fluid to said area of said skin from which said sample is to be extracted prior to forming said opening in said area of said skin from which said sample is to be extracted.

6. The method of claim 3, wherein heat is used to increase the availability of interstitial fluid to said area of said skin from which said sample is to be extracted prior to forming said opening in said area of said skin from which said sample is to be extracted.

7. The method of claim 4, wherein heat is used to increase the availability of interstitial fluid to said area of said skin from which said sample is to be extracted prior to forming said opening in said area of said skin from which said sample is to be extracted.

8. The method of claim 1, wherein said opening in said area of said skin from which the sample is to be extracted is formed by a rotating opening-forming device.

9. The method of claim 8, wherein said rotating opening-forming device is a drill.

10. The method of claim 8, wherein said rotating opening-forming device is a lancet.

11. The method of claim 1, wherein said extracted sample is analyzed by means of a glucose detector.

12. The method of claim 11, wherein said glucose detector employs an optical meter.

13. The method of claim 11, wherein said glucose detector employs an electrochemical meter.

14. The method of claim 8, wherein said rotating drill penetrates said skin to a depth of no more than 1.0 mm.

15. The method of claim 1, wherein said opening in said area of said skin from which the sample is to be extracted is formed by a laser.

16. The method of claim 1, wherein said interstitial fluid is obtained from a part of the body other than a finger.

17. The method of claim 1, wherein said interstitial fluid is obtained at a pain level lower than that experienced when a finger is pierced by a standard finger lancet.

18. An apparatus suitable for obtaining a sample of interstitial fluid for analysis in a diagnostic test, said apparatus comprising:

(a) a device for forming an unobstructed opening in an area of skin from which said sample is to be extracted;

(b) a vacuum pump for extracting said sample from said unobstructed opening in said area of said skin; and (c) a nosepiece having an end that contacts said area of said skin, said end being equipped with a seal, said seal surrounding an opening in said nosepiece, said opening allowing communication between said area of said skin and an interstitial fluid extraction chamber in said nosepiece, said seal preventing air from leaking into said interstitial fluid extraction chamber, so that said vacuum pump can provide sufficient suction action for increasing availability of interstitial fluid to said area of said skin from which said sample is to be obtained, for stretching said skin, and for extracting said sample of interstitial fluid from said unobstructed opening in said area of said skin.

19. The apparatus of claim 18, further including a housing.

20. The apparatus of claim 19, wherein said device for forming said unobstructed opening comprises a lancing assembly.

21. The apparatus of claim 18, wherein said device for forming said unobstructed opening is a laser.

22. The apparatus of claim 18, wherein said device for forming said unobstructed opening is a lancing assembly.

23. The apparatus of claim 22, wherein said lancing assembly comprises a lancet capable of being rotated.

24. The apparatus of claim 23, wherein said lancet is capable of being retracted after it forms said unobstructed opening in said skin.

25. The apparatus of claim 22, wherein said lancing assembly comprises a drill capable of being rotated.

26. The apparatus of claim 25, wherein said drill is capable of being retracted after it forms said unobstructed opening in said skin.

27. The apparatus of claim 18, further comprising a heating element.

28. The apparatus of claim 18, further comprising a glucose detector.

29. The apparatus of claim 28, wherein said glucose detector can utilize an electrochemical meter.

30. The apparatus of claim 28, wherein said glucose detector can utilize an optical meter.

31. The apparatus of claim 18, wherein said vacuum is applied through said opening in said nosepiece, said opening having an area up to 5 cm$^2$.

32. A method for obtaining a sample of interstitial fluid for a diagnostic test, said method comprising the steps of:

(1) first treating an area of the skin with vacuum or heat or both vacuum and heat to increase the availability of interstitial fluid at that area of the skin;

(2) then forming an unobstructed opening in the treated area of the skin; and (3) then extracting the sample of interstitial fluid from the unobstructed opening in the skin, with the aid of vacuum and stretching of the skin.

* * * * *